US00PP21960P2

(12) United States Plant Patent
Danziger

(10) Patent No.: US PP21,960 P2
(45) Date of Patent: May 31, 2011

(54) ***SUTERA* PLANT NAMED 'DANCOP36'**

(50) Latin Name: *Sutera cordata*
Varietal Denomination: DANCOP36

(75) Inventor: Gavriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 12/798,759

(22) Filed: Apr. 9, 2010

(51) Int. Cl.
*A01H 5/00* (2006.01)

(52) U.S. Cl. ..... Plt./485
(58) Field of Classification Search ..... Plt./485
See application file for complete search history.

*Primary Examiner* — June Hwu
*Assistant Examiner* — Louanne C Krawczewicz Myers
(74) *Attorney, Agent, or Firm* — Foley & Lardner LLP

(57) ABSTRACT

A new and distinct *Sutera cordata* plant named 'DANCOP36' particularly characterized by 5-petalled flowers, measuring about 2.4 cm in diameter and violet in color with a yellow-orange colored throat; semi-trailing, compact growth habit; early flowering response; and suitable for use with hanging basket planters, combination planters and ground cover under full sunlight-and slight shade.

2 Drawing Sheets

Latin name of the genus and species of the claimed plant: *Sutera cordata.*

Variety denomination: 'DANCOP36'.

BACKGROUND OF THE INVENTION

The present invention relates to a new and distinct cultivar of *Sutera* plant, botanically known as *Sutera cordata,* hereinafter referred to by the cultivar name 'DANCOP36'.

*Sutera,* of the Scrophulariaceae family, consists of annuals which are grown in most climate zones in the U.S., and only in zones 9 and 10 if it is a perennial plant.

The new *Sutera* 'DANCOP36' is a product of a planned breeding program conducted by the inventor, Gavriel Danziger, in Moshav Mishmar Hashiva, Israel. The objective of the breeding program is to develop a new *Sutera* variety with branched, semi-trailing growth habit and large, violet colored flowers.

The new *Sutera* 'DANCOP36' originated from open pollination by an unknown *Sutera* cultivar of the unpatented, female/seed parent, *Sutera cordata* designated cv. 07-621, in a controlled breeding program by the inventor in 2008 in Moshav Mishmar Hashiva, Israel. The new *Sutera* 'DANCOP36' was discovered and selected by the inventor as a single flowering plant within the progeny of the stated cross in a controlled environment in 2008 in Moshav Mishmar Hashiva, Israel.

Asexual reproduction of the new *Sutera* 'DANCOP36' by vegetative tip cuttings was first performed in August 2008 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DANCOP36', which in combination distinguish this *Sutera* as a new and distinct cultivar:

1. 5-petalled flowers, measuring about 2.4 cm in diameter and violet in color with a yellow-orange colored throat;
2. Semi-trailing, compact growth habit;

3. Early flowering response; and
4. Suitable for use with hanging basket planters, combination planters and ground cover under full sunlight-and slight shade.

Plants of the new *Sutera* 'DANCOP36' differ from plants of the plants of the female/seed parent, *Sutera cordata* designated cv. 07-621 (unpatented), in the characteristics described in Table 1.

TABLE 1

| Characteristic | New Cultivar 'DANCOP36' | Female Parent 'cv. 07-621' (unpatented) |
|---|---|---|
| Flower color | Violet | Lilac |
| Flower size | Large | Medium |
| Growth habit | Semi-trailing | Trailing |

Of the many commercial cultivars known to the present inventor, the most similar in comparison to the new *Sutera* 'DANCOP36' is *Sutera cordata* 'DANCOP29' (pending, U.S. Plant patent application Ser. No. 12/383,772). Plants of the new *Sutera* 'DANCOP36' differ from plants of *Sutera* 'DANCOP29', in the characteristics described in Table 2.

TABLE 2

| Characteristic | New Cultivar 'DANCOP36' | Comparison Cultivar 'DANCOP29' (pending, U.S. Ser. No. 12/383,772) |
|---|---|---|
| Growth habit | Semi-trailing | Trailing |
| Flower color | Violet | Light Blue |
| Plant height | Medium | Low |

BRIEF DESCRIPTION OF THE PHOTOGRAPHS

The accompanying photographs illustrate the overall appearance of the new *Sutera* 'DANCOP36' showing the colors as true as is reasonably possible with colored reproductions of this type. Colors in the photographs may differ slightly from the color value cited in the detailed botanical description which accurately describe the color of 'DANCOP36'.

DETAILED BOTANICAL DESCRIPTION

Figure 1:
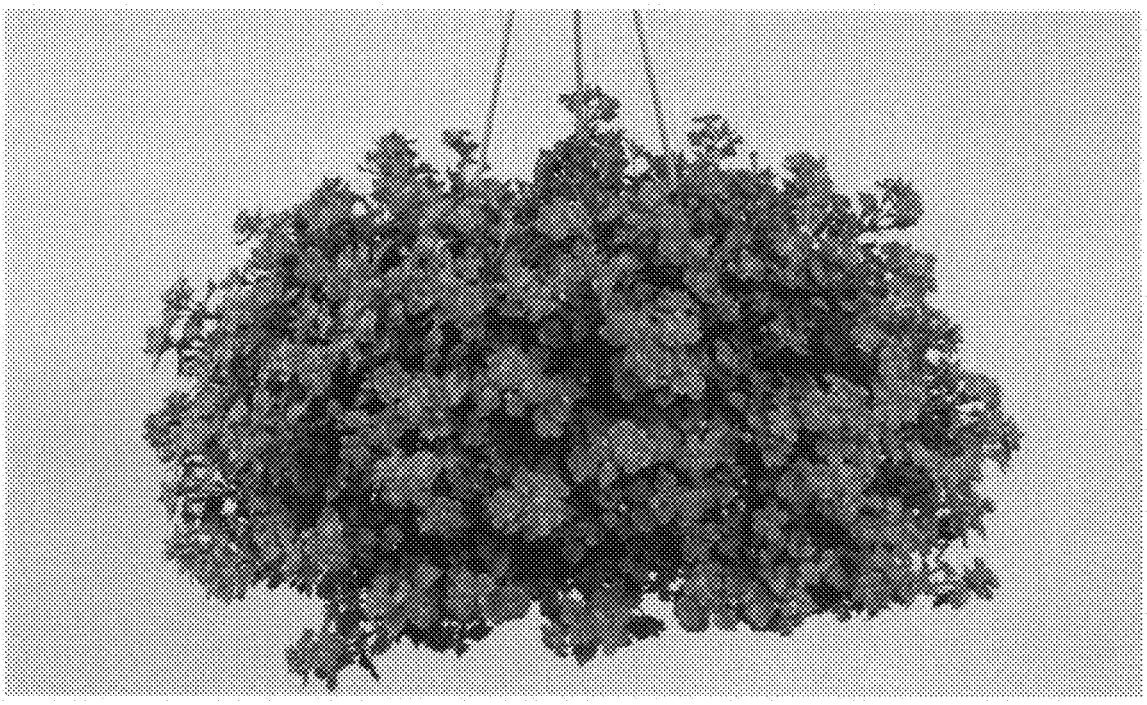
FIG. 1 shows a side view perspective a typical flowering plant of 'DANCOP36' in a hanging planter, at 3 months of age.
Figure 2:
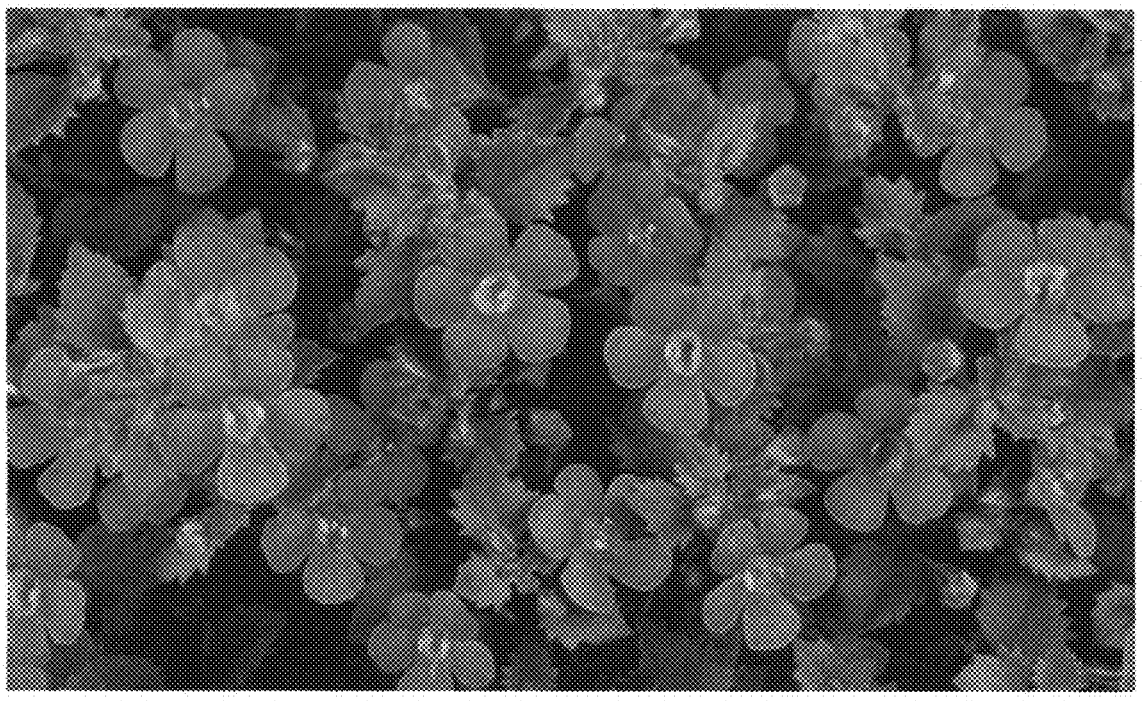
FIG. 2 shows a close-up view of the typical flowers, buds and leaves of 'DANCOP36', at 3 months of age.

The new *Sutera* 'DANCOP36' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Sutera* 'DANCOP36' as grown in a greenhouse in Moshav Mishmar Hashiva, Israel, under conditions which closely approximate those generally used in commercial practice. Plants were grown in a partially shaded (up to 50%) greenhouse, at temperatures between 16° C. (night) to 30° C. (day). A balanced fertilizer was provided with each watering, at levels of 150 ppm N.

Color references are made to The Royal Horticultural Society Colour Chart (R.H.S.), 2001 edition, except where general colors of ordinary significance are used. Color values were taken under daylight conditions at approximately (time) 12:00 noon in Moshav Mishmar Hashiva, Israel. The age of the plant described is 3 months.

Classification:

*Botanical.*—*Sutera cordata.*

Parentage:

*Female or seed parent.*—*Sutera cordata* cv. 07-621 (unpatented).

*Male or pollen parent.*—Open Pollination by unknown *Sutera cordata* cultivar.

Optimal growth conditions:

*Light intensities.*—Full sunlight or slight shade.

*Temperature.*—Day: 20° C. to 24° C. Night: 16° C. to 20° C.

*Temperature tolerance.*—Tolerant to a low temperature of about 5° C. and tolerant to a high temperature of about 30° C.

*Fertilization.*—A balanced fertilizer with level of 100 ppm Nitrogen.

*Growth regulators.*—Unnecessary.

Propagation:

*Type.*—Tip cuttings of side shoots.

*Rooting habit and description.*—Fine, fibrous roots.

*Time to initiate roots.*—About 7 to 10 days at 20° C.

*Time to produce a rooted cutting.*—About 14 days at 20° C.

Plant:

*General appearance and form.*—Height: About 13 cm. Spread: About 50 cm.

*Shape.*—Semi-trailing, compact growth habit.

*Vigor.*—Strong.

*Strength.*—Strong.

*Crop time.*—About 6 to 8 weeks for a flowering pot.

*Fragrance.*—None.

Lateral branches:

TABLE 3

| Branch characteristic | Primary | Secondary |
|---|---|---|
| Quantity Per Plant | About 6 | About 60 |
| Length | About 60 cm. | About 30 cm. |
| Diameter | About 2 mm. | About 1 mm. |
| Aspect: | About 90° | About 45° |
| Internode Length | About 2 cm. | About 1.5 cm. |
| Texture | Velvety | Velvety |
| Pubescence | Slightly pubescent | Slightly pubescent |
| Color | Green, RHS 137A | Green, RHS 137B |

Foliage:

*Arrangement and attachment.*—Opposite, petiolate.

*Leaf length.*—About 2.5 cm.

*Leaf width.*—About 1.5 cm.

*Overall shape of leaf.*—Ovate.

*Apex shape.*—Acute.

*Base shape.*—Acuminate.

*Margin.*—Crenate.

*Texture.*—Upper Surface: Slightly velvety. Under Surface: Slightly velvety.

*Pubescence.*—Upper Surface: Slightly pubescent. Under Surface: Slightly pubescent.

*Color of mature leaf.*—Upper Surface: Green, RHS 137A. Under Surface: Green, RHS 137B.

*Color of immature leaf.*—Upper Surface: Green, RHS 137A. Under Surface: Green, RHS 137B.

*Venation.*—Pattern: Pinnate. Color: Upper surface: Green, RHS 137A. Under Surface: Green, RHS 137B.

*Petiole.*—Length: About 5 mm. Diameter: About 2 mm. Color: Green, RHS 137A.

*Leaf fragrance.*—None.

Flower description:

*Natural flowering season.*—All year round in moderate climate. Flowering occurs between January and December outdoors in Israel.

*Flowering response time.*—About 5 weeks from planting.

*Flowering longevity.*—On the plant: Flowering of a single flower lasts for 7 days.

*Flower fragrance.*—None.

*Quantity of flowers and buds per plant.*—About 200.

*Flower bud* (*about* 2 *days prior to opening*).—Shape: Spatulate. Length: About 11 mm. Diameter: About 6 mm. Texture: Velvety. Color: Violet, RHS N87B.

*Flower type.*—Solitary, axillary.

*Flower form.*—Salverform.

*Flower symmetry.*—Radially symmetric.

*Orientation at opening.*—Slanted upward and outward.

*Corolla size.*—Diameter (spread): About 24 mm. Diameter at lobes: About 24 mm. Overall flower height: About 10 mm. Length of corolla tube: About 9 mm. Diameter of corolla tube: About 4 mm.

*Petals.*—Quantity: 5. Length: About 9 mm. Width: About 8 mm. Overall shape: Rounded and gameopetalous. Apex: Rounded. Base: Fused. Margin: Entire. Texture (upper & under surfaces): Slightly velvety. Color: Upper surface, when opening: Violet, RHS N87A. Upper surface, opened flower: Violet, RHS N87B. Under Surface, when opening: Violet, RHS N87B. Under Surface, opened flower: Violet, RHS N87C. Corolla throat color: Yellow-orange, RHS 21A.

*Calyx.*—Sepals: Quantity: 5. Length: About 7 mm. Width: About 1 mm. Overall shape: Linear. Apex: Acute. Base: Fused. Margin: Entire. Texture: Upper surface: Velvety. Under Surface: Velvety. Upper surface color: Green, RHS 137C. Under Surface color: Green, RHS 137C. Anthocyanin pigmentation of calyx limb: Absent. Pedicel: Aspect: Slanted upward. Length: About 10 mm. Diameter: About 1 mm. Angle: About 45°. Texture: Velvety. Color: Green, RHS 137A.

Reproductive organs:

*Androecium.*—Stamen: Number: 4. Arrangement: Didynamous. Type: Basifixed. Dehiscence of stamens: Extrorse. Color: Yellow-orange, RHS 21C. Anthers: Shape: Cylinder. Length: About 1 mm. Color: Yellow-orange, RHS 21C. Filaments: Length: About 10 mm. Color: Yellow-green, RHS 150D. Pollen: Amount: Moderate. Color: Yellow-orange, RHS 21 C. Pollination requirements: Young, active pollen, and receptive, open stigma.

*Gynoecium.*—Pistils: Quantity: 1. Length: About 11 mm. Stigma: Shape: Undulate. Width: About 1 mm. Color: Yellow-green, RHS N144 B. Style: Shape: Terete. Length: About 9 mm. Ovary: Shape: Ellipsoid. Position: Superior. Length: About 1 mm. Width: About 1 mm. Color: Green, RHS 137C.

Seeds:

*Quantity per fruit.*—About 20.

*Shape.*—Elliptic.

*Length.*—About 1 mm.

*Width.*—About 0.5 mm.

*Texture.*—Rough.

*Color.*—Grayed-Orange, RHS 166C.

Fruit:

*Type.*—Capsule.

*Shape.*—Ellipsoid.

*Length.*—About 5 mm.

*Width.*—About 2 mm.

*Texture.*—Rugose.

*Color.*—Gray-Brown, RHS N199C.

Disease/pest resistance: Good.

Disease/pest susceptbility: Low.

What is claimed is:

1. A new and distinct *Sutera cordata* plant named 'DANCOP36', substantially as illustrated and described herein.

* * * * *